US007262269B2

(12) United States Patent
Lam et al.

(10) Patent No.: US 7,262,269 B2
(45) Date of Patent: *Aug. 28, 2007

(54) METHOD FOR SCREENING COMBINATIONAL BEAD LIBRARY; LIGANDS FOR CANCER CELLS

(75) Inventors: Kit S. Lam, Davis, CA (US); Derick H. Lau, Gold River, CA (US)

(73) Assignee: The Regents of University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/682,659

(22) Filed: Oct. 8, 2003

(65) Prior Publication Data

US 2004/0096906 A1 May 20, 2004

Related U.S. Application Data

(63) Continuation-in-part of application No. 10/032,678, filed on Oct. 26, 2001, now Pat. No. 6,670,142.

(51) Int. Cl.
*C07K 5/00* (2006.01)
*C40B 30/04* (2006.01)

(52) U.S. Cl. .................. 530/317; 530/321; 530/328
(58) Field of Classification Search ................ 530/317, 530/328, 321
See application file for complete search history.

(56) References Cited

U.S. PATENT DOCUMENTS

| 5,510,240 | A | 4/1996 | Lam | |
|---|---|---|---|---|
| 5,635,598 | A | 6/1997 | Lebl | |
| 5,650,489 | A | 7/1997 | Lam | |
| 5,651,943 | A | 7/1997 | Lam | |
| 5,840,485 | A | 11/1998 | Lebl | |
| 5,858,670 | A | 1/1999 | Lam | |
| 5,888,497 | A | 3/1999 | Jain | |
| 6,242,211 | B1 | 6/2001 | Peterson | |
| 6,784,153 | B1 * | 8/2004 | Rajotte et al. | .................. 514/2 |
| 6,933,281 | B2 * | 8/2005 | Ruoslahti et al. | ............. 514/15 |
| 2001/0005578 | A1 | 6/2001 | Prusiner | |
| 2004/0170955 | A1 * | 9/2004 | Arap et al. | ..................... 435/5 |

FOREIGN PATENT DOCUMENTS

WO    WO9827231    6/1998

OTHER PUBLICATIONS

Journal of the American Chemical Society (2002), 124(26), 7678-80, Liu et al.*
Liu, Gang, Yemei Fan, James R. Carlson, Zhan-Gong Zhao, and Kit S. Lam. "Solution-Phase Synthesis of a 1,5-Dialkylamino-2, 4-dinitrobenzene Library and the Identification of Novel Antibacterial Compounds from This Library." *J. Comb. Chem* 2, No. 5 (Aug. 3, 2000): 467-474.

Lam, Kit S. "Application of combinatorial library methods in cancer research and drug discovery." *Anti-Cancer Drug Design* 12 (1997): 145-167.
Cabilly, S., ed. *Methods in Molecular Biology*, vol. 87: *Combinatorial Peptide Library Protocols*, chap. 1 and 2. Totowa, New Jersey: Humana Press, Inc.
Lebl, Michal, Viktor Krchňák, Nikolai F. Sepetov, Bruce Seligmann, Peter Strop, Stephen Felder, and Kit S. Lam. "One-Bead-One-Structure Combinatorial Libraries." *Biopolymers (Peptide Science)* 37 (1995): 177-198.
Liu, Gang, and Kit S. Lam. One-bead one-compound combinatorial library method. In *Combinatorial Chemistry—A Practical Approach*. Edited by Hicham Fenniri. Oxford University Press.
Lam, Kit S., Sydney E. Salmon, Evan M. Hersh, Victor J. Hruby, Wieslaw M. Kazmierski, and Richard J. Knapp. "A new type of synthetic peptide library for identifying ligand-binding activity." *Nature* 354 (Nov. 7, 1991): 82-84.
Lam, Kit S. and Michal Lebl. "Selectide Technology: Bead-Binding Screening." *Methods: A Companion to Methods in Enzymology* 6 (1994): 372-380.
Lam, Kit S., Zhan-Gong Zhao, Shelly Wade, Viktor Krchňák, and Michal Lebl. "Identification of Small Peptides That Interact Specifically With a Small Organic Dye." *Drug Development Research* 33 (1994): 157-160.
Wu, Jinzi, Qingyan N. Ma, and Kit S. Lam. "Identifying Substrate Motifs of Protein Kinases by a Random Library Approach." *Biochemistry* 33 (1994): 14825-14833.
Smith, M. H., A. A. Nuara, J. G. Egen, D. B. Sirjani, K. S. Lam, and W. J. Grimes. "Baculoviral expressed HLA class I heavy chains used to screen a synthetic peptide library for Allele-Specific peptide binding motifs." *Molecular Immunology* 35 (1998): 1033-1043.
Pennington, Michael E., Kit S. Lam, and Anne E. Cress. "The use of a combinatorial library method to isolate human tumor cell adhesion peptides." *Molecular Diversity* 2 (1996): 19-28.
Lam, Kit S., Michal Lebl, and Viktor Krchňák. "The 'One-Bead-One-Compound' Combinatorial Library Method." *Chem Rev* 97 (1997): 411-448.
Lam, Kit S. Synthetic peptide and nonpeptide libraries. *Encyclopedia of Molecular Biology and Molecular Medicine* 5 (1996): 516-524.
Lam, Kit S., Thomas Sroka, Man-Ling Chen, Yu Zhao, Qiang Lou, Jinzi Wu, Zhan-Gong Zhao. Application of "one-Bead One-Compound" Combinational Library Methods in Single Transduction Research. *Life Sciences* 62, Nos. 17/18 (1998): 1577-1583.

(Continued)

*Primary Examiner*—T. D. Wessendorf
(74) *Attorney, Agent, or Firm*—Audrey A. Millemann; Weintraub Genshlea Chedia

(57) ABSTRACT

The invention includes a cell-growth-on-bead assay for screening a one-bead-one-compound combinatorial bead library to identify synthetic ligands for cell attachment and growth or proliferation of epithelial and non-epithelial cells. Cells are incubated with a compound bead library for 24 to 72-hours, allowing them to attach and grow on the beads. Those beads with cells growing are removed, and the ligand on the bead is identified. Also provided are ligands specific for cancer cells.

3 Claims, 2 Drawing Sheets

OTHER PUBLICATIONS

Lam, Kit S., Douglas Lake, Sydney E. Salmon, John Smith, Man-Ling Chen, Shelly Wade, Farid Abdul-Latif, Richard J. Knapp, Zuzana Leblova, Ronald D. Ferguson, Viktor Krchnak, Nikolai F. Sepetov, Michal Lebl. A One-Bead One-Peptide Combinatorial Library Method for B-Cell Epitope Mapping. *METHODS: A Companion to Methods in Enzymology* 9 (1996): 482-493.

Park, Steven, Renil Manat, Brian Vikstrom, Nail Amro, and Kit S. Lam. "Identification of Peptide Ligands for α4β1 Integrin Receptor as Potential Targeting Agents for Non-Hodgkin's Lymphoma." *Peptides: The Wave of the Future*. 2nd International Peptide Symposium in conjuction with the 17th American Peptide Symposium. Jun. 9-14, 2001, San Diego, CA.

Clark, Peter. 1998. "Micropatterning cell adhesiveness" in *Immobilized Biomolecules in Analysis—A Practical Approach*. Edited by Tony Cass and Frances S. Ligler, Oxford University Press.

DeRoock, Ian B., Michael E. Pennington, Thomas C. Sroka, Kit S. Lam, G. Tim Bowden, Elisabeth L. Bair, and Anne E. Cress. "Synthetic Peptides Inhibit Adhesion of Human Tumor Cells to Extracellular Matrix Proteins." *Cancer Research* 61 (Apr. 15, 2001) 3308-3313.

Lau, Derick H., Linlang Guo, Ruiwu Liu, Aimin Song, Chunkui Shao, and Kit S. Lam. "Identifying peptide ligands for cell surface receptors using cell-growth-on-bead assay and one-bead one-compound combinatorial library." *Biotechnology Letters* 24 (2002) 497-500.

Mařík, Jan, Derick H. Lau, Aimin Song, Xiaobing Wang, Ruiwu Liu, Kit S. Lam. "Magnetization of Large Polystyrene Peptide Beads for Capturing and Expanding Cancer Cells." *Elsevier Science* (Feb. 7, 2003).

Aina, Olulanu H., Thomas C. Sroka, Man-Ling Chen, and Kit S. Lam. "Therapeutic Cancer Targeting Peptides." Published online Oct. 7, 2002 in *Wiley Interscience* (www.interscience.wiley.com).

Liu, Ruiwu, Jan Mařík, and Kit S. Lam. "A Novel Peptide-Based Encoding System for 'One-Bead One-Compound' Peptidomimetic and Small Molecule Combinatorial Libraries." *J. Am. Chem Sci.* 124 (2002) 7678-7680.

Cardareli, Pina M., et al. "The collagen receptor alpha-2-beta-1, from MG-63 and HT1080 cells, interacts with a cyclic RGD peptide." *Journal of Biological Chemistry* 267 (1992) 32: 23159-23164.

Durcova, G., et al. "Immunomagnetic Isolation of Mouse Embryonic Stem Cells from Heterogeneous Cell Population." *Theriogenology* 47 (1997) 1: 242.

Krueger, W., et al. "Purging in Der Knochenmark- und Stammzell Transplantationl Purging in Bone Marrow and Stem Cell Transplantation." *Laboratoriumsmedizien, Kirchheim, De* 20 (1996) 4: 210-220.

Yang, Yi, et al. "LPAM-1 (integrin alpha4beta7)-ligand binding: Overlapping binding sites recognizing VCAM-1, MAdCAM-1 and CS-1 are blocked by fibrinogen, a fibronectin-like polymer and RGD-like cyclic peptides." *European Journal of Immunology* 28 (Mar. 1998) 3: 995-1004.

European Patent Application, pub. No. EP 0 332 912 A2 (Jolla Cancer Res Found) (published Sep. 20, 1989), "Inhibition of cell migration with synthetic peptides."

Aina, Olulanu H., et al. "Identification of Novel Targeting Peptides for Human Ovarian Cancer Cells Using OBOC Combinatorial Libraries." Draft publication submitted to *Molecular Cancer Therapeutics*, in about Mar. 2005.

Song, Aimin, Jinhua Zhang, Carlito B. Lebrilla, and Kit S. Lam. "A Novel and Rapid Encoding Method Based on Mass Spectrometry for 'One-Bead-One-Compound' Small Molecule Combinatorial Libraries." *J. Am. Chem. Soc.* 125 (2003): 6180-6188.

Derick Lau, Linlang Guo, Ruiwu Liu, Jan Marik, Kit Lam. "Peptide Ligands Targeting Integrin—3B1 in Non-Small Lung Cancer." *Lung Cancer* (2006) 52, 291-297.

Olulanu H. Aina, Jan Marik, Regina Gandour-Edwards, Kit S. Lam. "Near-Infrared Optical Imaging of Ovarian Cancer Xenografts with Novel ∝ 3-Integrin Binding Peptide OA02." *Molecular Imaging* (Oct. 2005) vol. 4, No. 4, pp. 439-447.

Olulanu H. Aina, Jan Marik, Ruiwu Liu, Derick H. Lau, and Kit S. Lam. "Identification of Novel Targeting Peptides for Human Ovarian Cancer Cells Using "One-Bead One-Compound" Combinatorial Libraries." *Molecular Cancer Therapeutics*. (May 2005) 4(5), pp. 806-813.

* cited by examiner

METHOD FOR SCREENING COMBINATIONAL BEAD LIBRARY; LIGANDS FOR CANCER CELLS

This application is a continuation-in-part of U.S. application Ser. No. 10/032,678 filed on Oct. 26, 2001, now U.S. Pat. No. 6,670,142.

The United States Government has a paid-up license in this invention and the right in limited circumstances to require the patent owner to license others on reasonable terms as provided for by the terms of grant number R33 CA89706 awarded by the National Cancer Institute and the National Institutes of Health.

BACKGROUND OF THE INVENTION

1. Field of the Invention

The invention relates to screening methods for one-bead-one-compound combinatorial libraries and includes a screening assay that uses live cells to identify synthetic ligands that promote attachment and growth or proliferation of epithelial and non-epithelial cells. Also included are ligands specific for epithelial and non-epithelial cancer cells.

2. Description of Related Art

One-bead-one-compound combinatorial bead libraries (see Lam, Kit S. et al. "A new type of synthetic peptide library for identifying ligand-binding activity." *Nature* 354 (1991): 82-84), such as one-bead-one-compound peptide libraries, are being used to study cell adhesion properties of cancer cells. Using random peptide bead libraries and suspended cancer cells, peptide ligands that promote cell attachment have been identified for lymphoma (Park, Steven, Renil Manat, Brian Vikstrom, Nail Amro, and Kit S. Lam. "Identification of peptide ligands for $\alpha 4\beta 1$ integrin receptor as potential targeting agents for non-Hodgkin's lymphoma," abstract in Peptides: *The Wave of the Future,* 2nd International Peptide Symposium in conjunction with the $17^{th}$ American Peptide Symposium, San Diego, Calif. (Jun. 9-14, 2001)) and prostate cancer cell lines (Pennington, Michael E., Kit S. Lam and Anne E. Cress. "The use of a combinatorial library method to isolate human tumor cell adhesion peptides." *Molecular Diversity* 2 (1996): 19-28; DeRoock, Ian B., Michael E. Pennington, Thomas C. Sroka, Kit S. Lam, G. Tim Bowden, Elisabeth L. Bair, and Anne E. Cress. "Synthetic Peptides Inhibit Adhesion of Human Tumor Cells to Extracellular Matrix Proteins." *Cancer Research* 61 (Apr. 15, 2001): 3308-13).

In the existing methods, live cells in suspension are incubated for about one to four hours with a bead library, and the library is then screened for beads with peptide ligands that promote cell attachment. This is done by visual selection the beads are examined under a dissecting microscope and those beads with attached cells are removed using a micropipet. Further steps are then performed to confirm that the removed beads are in fact capable of binding the particular type of cells tested. Then, the peptides on those beads are sequenced. (See Pennington et al., "Use of a combinatorial library method," 19-28.)

In another existing method of testing live cells for peptide ligands that affect cell growth on culture plates, a bead library is prepared having selectively cleavable peptides such that a proportion of the peptide on each bead is attached to the bead by a cleavable linker. When the library is treated with a cleaving agent, enough of the peptides are released from the beads to cause the biological effect, and the rest of the peptides remain bound to the beads to allow for later sequencing. Suspended cells are incubated in tissue culture wells with a few beads and with peptides released from the beads. The effect of the released peptides on the cells (inhibition or stimulation of cell growth) is determined, and the corresponding beads are removed. The sequences of the attached peptides are then determined. (See U.S. Pat. No. 5,510,240, issued Apr. 23, 1996 to Lam, Kit S. et al.)

The existing methods, however, are not satisfactory in certain cases. The methods are difficult to use with epithelial cells, which include the majority of solid cancer cell cultures, such as lung cancer cells, that exist as adherent cultures rather than as suspended cells. With incubation periods of only a few hours, these cells are often only weakly attached to the beads and may easily fall off, rendering the screening method less accurate because some beads with attached cells are missed. Also, the existing methods may not detect cell surface receptors that may be altered by trypsin and/or EDTA. Trypsinization is commonly used to separate tissues or cell cultures into a single-cell suspension for testing with a combinatorial library. The treatment with trypsin may eliminate some, or alter the conformation of, cell surface receptors. In addition, the existing methods do not select for ligands that promote cell growth or proliferation, but, rather, for ligands involved in cell attachment, particularly short-term attachment.

Thus, there is a need for a screening assay that is specific and sensitive, works well with epithelial cells, can be used to detect cell surface receptors susceptible to trypsin, and selects for ligands that promote not only cell attachment, but also cell growth or proliferation.

SUMMARY OF THE INVENTION

The present invention is directed to a method for screening a combinatorial bead library for ligands that promote the attachment and growth or proliferation of epithelial and non-epithelial cells. The method satisfies the need for an assay that is specific and sensitive, that can be used to detect cell surface receptors susceptible to trypsin, and that can identify ligands that promote cell growth and proliferation. The method comprises introducing a suspension of live cells to a combinatorial library of small molecules, peptides, or other types of molecules, incubating the cells with the library for about 24 to 72 hours, identifying a solid phase support of the library with cells growing on the support, isolating the solid phase support, and determining the chemical structure of the compound attached to that solid phase support.

The invention also includes ligands specific for cell attachment and growth or proliferation of epithelial and non-epithelial cancer cells.

BRIEF DESCRIPTION OF THE DRAWINGS

FIG. 1 is a diagram depicting the steps of the cell-growth-on-bead assay as used with epithelial cells.

DETAILED DESCRIPTION OF THE PREFERRED EMBODIMENTS

The invention includes a method, referred to as the cell-growth-on-bead assay, for screening a one-bead-one-compound combinatorial bead library for ligands that promote cell attachment and growth or proliferation. Ligands that promote cell attachment and growth or proliferation of epithelial and non-epithelial cancer cells are also described.

Cell-Growth-on-Bead Assay

The cell-growth-on-bead assay includes the following steps. A one-bead-one-compound combinatorial library is prepared. The library is preferably synthesized using the "split synthesis" approach described in Lam et al., "A new type of synthetic peptide library," 82-84. The compounds of the library may be small molecules, peptides, or other types of molecules. An example of a suitable library is a peptide library containing cXXXXXXc peptides, where "c" is D-cysteine which provides intramolecular cyclization by disulfide bonding, and "X" is any L, D, unnatural, or modified amino acid. A suitable solid phase support, such as beads or discs made of polystyrene, agarose, acrylamide, glass, plastic, or paramagnetic substances, is used. Polystyrene beads have been found satisfactory. A standard synthetic solid phase peptide synthesis method, such as fluorenylmethyoxycarbonyl (Fmoc) chemistry or t-butyloxycarbonyl (Boc) chemistry, is used.

Figure 1A:
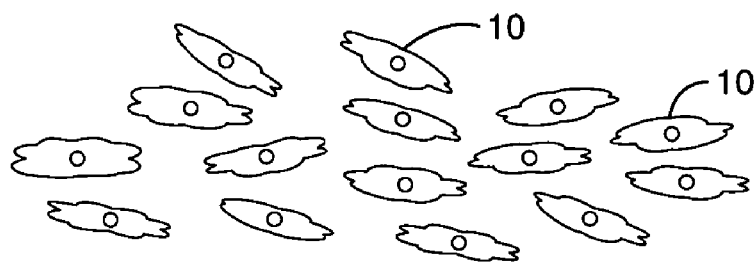
FIG. 1A shows attached epithelial cells.
Figure 1B:
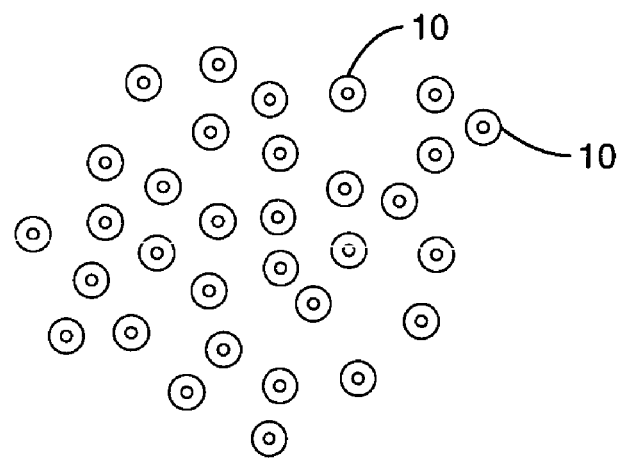
FIG. 1B shows the detached epithelial cells of FIG. 1A in suspension.

A suspension of live mammalian cells is prepared according to methods known to those skilled in the art. The cells may be epithelial or non-epithelial cells and may be cancerous or non-cancerous. Human cancer cells from a cell line or derived from biopsy specimens or body fluid of cancer patients may be used. FIG. 1 shows the method as used with epithelial cells. FIG. 1A shows attached epithelial cells 10. FIG. 1B shows the same cells 10 in suspension.

Figure 1C:
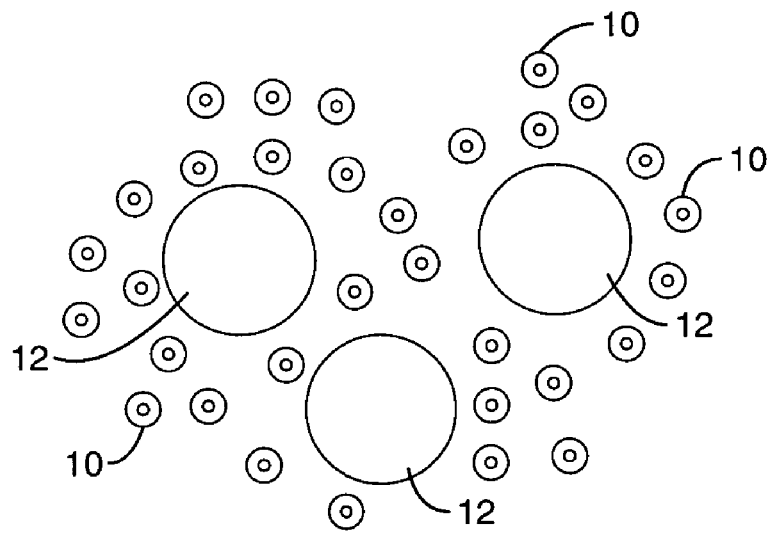
FIG. 1C shows the epithelial cells being mixed with the beads of the bead library.

Suspended live cells 10 are mixed with the library in culture medium, as shown in FIG. 1C, and distributed into culture plates. The ratio of cells to beads is preferably about 10:1, but can range from about 1:1 to 100:1. The suspension of cells 10 and beads 12 is mixed gently for sufficient time to assure contact of beads 12 with suspended cells 10. The culture plates are incubated in a tissue culture incubator at about 4° C. to about 37° C., preferably 37° C., for a period of about 24 to about 72 hours. The suspension of cells 10 and beads 12 may be kept still or mixed, either continuously or intermittently, during the incubation period.

Figure 1D:
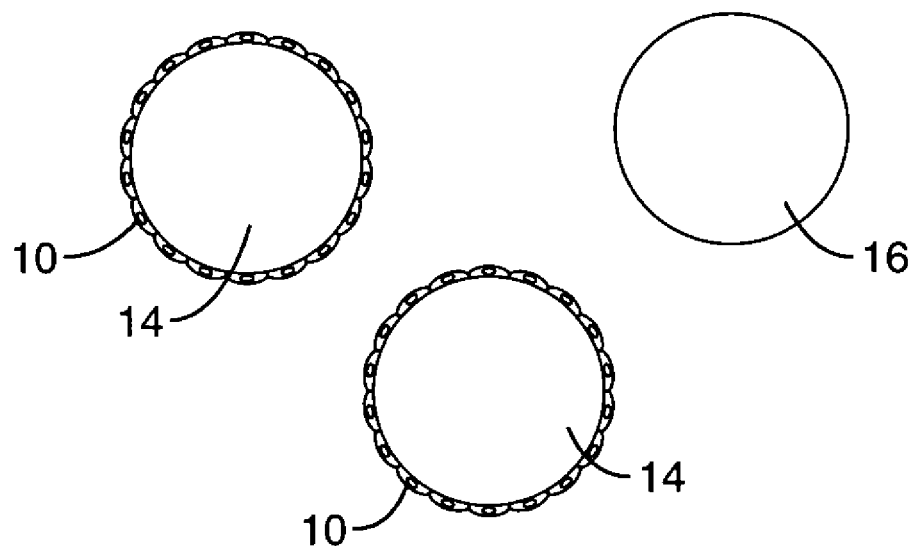
FIG. 1D shows a top view of three beads, in which two beads have a monolayer of cells growing on the bead.
Figure 1E:
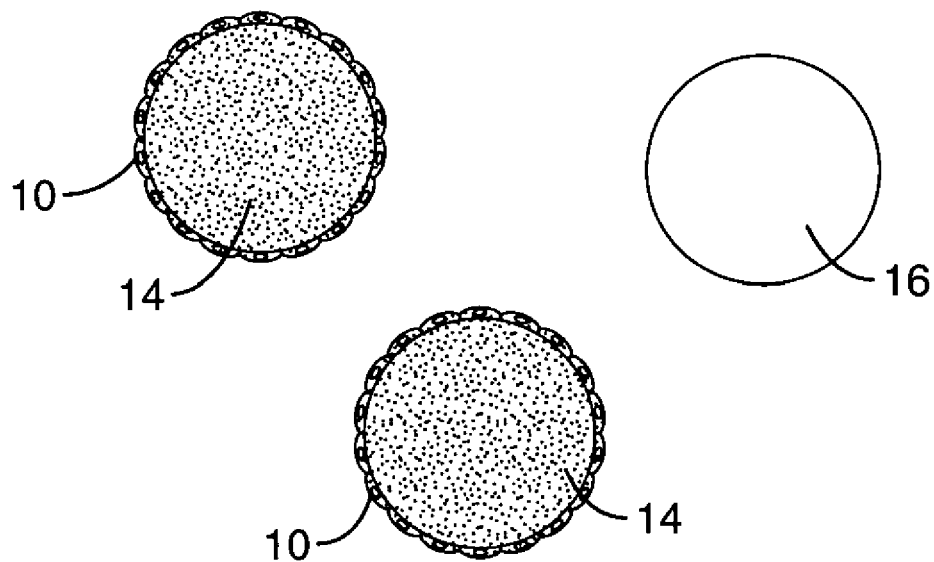
FIG. 1E shows a top view of the three beads of FIG. 1D, after staining, in which the two beads with a monolayer of cells growing on the bead are stained, and the one bead without any cells is not stained.

After the incubation period, beads 12 are observed under a dissecting microscope. The presence of an increased number of cells 10 or beads 14 covered with a monolayer of cells, as shown in FIG. 1D, evidences cell growth or proliferation. These beads 14 (referred to as "positive" beads) are removed from the culture plates. A tetrazolium dye that stains live, but not dead, cells can be used to facilitate the identification and removal of the positive beads. If a dye is used, all of the beads are removed after the incubation period and resuspended in fresh medium in new culture plates. The dye is added. The plates are then incubated in a tissue culture incubator at 25° C. to 37° C. for about one to four hours. Live cells 10 convert the dye to a colored metabolite, which results in beads 14 with attached cells appearing colored, allowing them to be easily distinguished from beads 16 without attached cells, which appear colorless, as shown in FIG. 1E. Other dyes that stain live cells can also be used. After positive beads 14 are removed from the plates, attached cells 10 are separated from the beads. This can be done with the addition of a chaotrophic agent, such as 8 M guanidine hydrochloride, or a protease, such as trypsin.

The chemical structure of the compound (i.e. ligand) on each isolated positive bead 14 is then determined. If the combinatorial library used was a peptide library, then the amino acid sequence of the ligand is preferably determined with an automated protein sequencer, such as the Procise 494 (Applied Biosystems, Foster City, Calif.). Alternatively, the peptide can be released via a cleavable linker and the amino acid sequence determined by mass spectroscopy. If the ligand on the bead consists of a small molecule, then mass spectroscopy or encoding strategies can be used. See Liu, Ruiwu, Jan Marik, and Kit S. Lam. "A novel peptide-based encoding system for 'one-bead-one-compound' peptidomimetic and small molecule combinatorial libraries." *J. Am. Chem. Soc.* 124 (2002) 7678-7680; Song. Aimin, Jinhua Zhang, Carlito B. Lebrilla, and Kit S. Lam. "A novel and rapid encoding method based on mass spectrometry for 'one-bead-one-compound' small molecule combinatorial libraries." *J. Am. Chem. Soc.* 125 (2003) 6180-6188.

Using the cell-growth-on-bead assay, ligands that promote cell attachment and growth or proliferation have been identified for epithelial and non-epithelial cancer cells, including lung cancer, ovarian cancer, brain cancer, liver cancer, and pancreatic cancer. Structure/activity relationship studies have resulted in the identification of ligands for epithelial and non-epithelial cancer cells having the general structure of cXGXGXXc, in which "c" is D-cysteine; "X" is any L, D, unnatural, or modified amino acid; and "G" is glycine. Small molecule ligands and peptidomimetic ligands have also been identified.

Definitions

In addition to standard abbreviations for amino acids, the following abbreviations for amino acids are used: HoSer is homoserine, Cit is citruline, HoCit is homocitruline, Hyp is hydroxyproline, Aad is 2-aminohexanedioic acid, Lys(Ac) is ε-acetyllysine, 4-Pal is 3-(4-pyridyl)alanine, D-3-Pal is D-3-(3-pyridyl)alanine, Pra is propargylglycine, D-Pra is D-propargylglycine, Aib is 2-aminoisobutyric acid, Phe(4-CN) is 4-cyanophenylalanine, Tyr(3-$NO_2$) is 3-nitrotyrosine, Tyr(Me) is O-methyltyrosine, Phe(4-$NO_2$) is 4-nitrophenylalanine, Bug is tertiary butylglycine, Ach is 1-amino-1-cyclohexanecarboxylic acid, Tyr(3,5-I) is 3,5-diiodotyrosine, Aic is 2-aminoindane-2-carboxylic acid, Phe(3-Cl) is 3-chlorophenylalanine, Chg is cyclohexylglycine, Bta is 3-benzothienylalanine, Bpa is 4-benzoylphenylalanine, Phe(3,4-Cl) is 3,4-dichlorophenylalanine, Hyp(Bzl) is O-benzylphenylalanine, Cha is cyclohexylalanine, Abu is 2-aminobutyric acid, Nva is norvaline, Phg is phenylglycine, Ach is 1-amino-1-cyclohexanecarboxylic acid, Nle is norleucine, Phe(4-Me) is 4-methylphenylalanine, HoPhe is homophenylalanine, 2-Nal is 3-(2-naphtyl)alanine, 1-Nal is 3-(1-naphtyl)alanine, Tyr(3,5-I) is 3,5-diiodotyrosine, Acdt is 4-amino-4-carboxy-1,1-dioxo-tetrahydrothiopyran, Dpr is 2,3-diaminopropionic acid, and D,L-beta-Fal(2) is D,L-3-(furan-2-yl)-3-amino-propionic acid.

EXAMPLE 1

A one-bead-one-peptide combinatorial library, containing random cXXXXXXc peptides, was prepared using the "split synthesis" method of Lam et al., "A new type of synthetic peptide library," 82-84. The random peptide library contained $19^6=4.7 \times 10^7$ possible permutations of the formula cXXXXXXc, where "c" is D-cysteine, and "X" is one of 19 natural L-amino acids. In this example, and in all other cases where a peptide or peptidomimetic library is used, the D-cysteines provide intramolecular cyclization by disulfide bonding.

TentaGel polystyrene beads, with a diameter of 80 μm and with grafted polyethylene glycol of 0.25 mmol/g, were used as a solid phase support (Rapp Polymere, Germany). A synthetic solid phase method using fluorenylmethyoxycarbonyl (Fmoc) chemistry was adapted for synthesizing the peptide bead library.

The non-small-cell lung cancer cell line, A549 (American Type Culture Collection, Manassas, Va.), was used. The cell line was maintained in appropriate culture media as recommended by American Type Culture Collection. Cells were grown to confluency in DMEM culture medium supplemented with 10% fetal calf serum. Attached cells were recovered with trypsin/EDTA, washed, and resuspended as single cells in culture medium.

About 150,000 peptide beads were mixed with approximately one million suspended cells in 15 ml of culture medium and distributed into six 3-cm culture plates. The culture plates were agitated gently at about 100 rpm for about 10 minutes. The culture plates were then incubated in a tissue culture incubator at 37° C. for about 24 hours to about 72 hours.

A dissecting microscope was used to examine the beads at about 24, 48, and 72 hours. After about 24 to 72 hours, beads with a monolayer of cells were observed. Out of a library of about 150,000 beads, about 20 to 30 beads typically exhibited cell growth.

At the end of the incubation period, all of the beads were removed and resuspended in fresh medium in a new culture plate. An MTT ([3-(4,5-dimethylthiazol-2-yl)-2,5-diphenyl] tetrazolium bromide) (Sigma, St. Louis, Mo.) dye solution was added to each culture plate to a final concentration of 0.5 mg/ml. The plates were incubated in a tissue culture incubator at 37° C. for about two hours to allow the purple color to develop. Each purple-colored peptide bead was isolated and removed. The attached cells were separated from the beads with 8 M guanidine hydrochloride.

The amino acid sequence of each isolated peptide bead was determined using an automated Procise 494 protein sequencer (Applied Biosystems, Foster City, Calif.). Several consensus peptide sequences were determined, one of which was cNGRGEQc. This peptide was resynthesized on beads, which were then rescreened with the A549 cells using the assay of the invention. Virtually all of the beads with this sequence exhibited cell attachment and growth on their surfaces.

To test the sensitivity of the assay, blank beads and a linear XXXXXX peptide bead library of 150,000 beads were each spiked with 10 positive peptide beads carrying the sequence cNGRGEQc. These libraries were each screened with the A549 cells. The peptide beads with the sequence of cNGRGEQc were isolated with a recovery rate of 90% to 100% in two separate experiments.

To test cell type specificity of beads carrying the peptide ligand cNGRGEQc, cell growth of two other non-small-cell lung cancer cell lines, Calu-1 and Hi 78, was observed on 70% to 90% of the peptide beads. On the other hand, cell growth was observed on only 10% of the peptide beads with the non-malignant bronchoepithelial cell line, HBE-1. Thus, the cNGRGEQc peptide is a ligand specific for promoting cell attachment and growth of malignant cells of the lung.

Through additional secondary library screening and structure/activity relationship studies, other ligands for epithelial cells have been identified, including the following:

c-D-G-Chg-G-A-N-c; c-N-G-Bpa-G-Q-M-c; c-N-G-Acdt-G-D-Bpa-c; cNGTGDGc;

cNGQGAGc; cNGYGSFc; c-N-G-Nle-G-Y-G-c; cNGM-GAYc; cNGQGEQc;

cRGNGTDc; cNGQGPLc; cNGLGRSc; cDGMGSNc; cNGLGQYc; and cNGYGTTc.

EXAMPLE 2

The method as described in Example 1 was performed, except that the combinatorial peptide library was screened with a different type of epithelial cancer cells, the ovarian cancer cell line CaOV3 (American Type Culture Collection).

As described in Example 1, after culturing for about 24 to 72 hours, beads with a monolayer of cells were observed. These positive beads were isolated and the amino acid sequence of each positive bead was determined, as described in Example 1.

The following ligands were identified: cDGLGDDc and cDGWGPNc.

EXAMPLE 3

The method as described in Example 1 was performed, except that a different combinatorial library was used and different types of epithelial cancer cells were used. A one-bead-one-compound combinatorial peptide library was prepared according to the method described in Example 1, with the following formula: $cX_2GX_4GX_6X_7c$, where "c" is D-cysteine; "G" is glycine; $X_2$ is D,d,N, n, S,Q,q,T, HoSer, Cit, E, e, HoCit, Hyp, Aad, Lys(Ac), A, 4-Pal, D-3-Pal, Pra, D-Pra, Y, Aib, M, Phe(4-CN), Tyr(3-NO$_2$), Tyr(Me), Phe(4-NO$_2$), Bug, Ach, Tyr(3,5-I), Aic, Phe(3-Cl), Chg, Bta, Bpa, Phe(3,4-Cl), Hyp(Bzl), or Cha; and $X_4$, $X_6$ and $X_7$ are N, S, Q, T, HoSer, Cit, HoCit, Hyp, H, A, Pal, D-3-Pal, Pra, R, Y, Aib, Abu, P, M, V, Nva, Tyr(3-NO$_2$), W, Phg, Phe(4-NO$_2$), Bug, I, Ach, L, Nle, Phe(4-Me), Aic, Phe(3-Cl), HoPhe, Chg, Bta, Bpa, 2-Nal, 1-Nal, Phe(3,4-Cl), Hyp(Bzl), or Cha.

The peptide library was screened with one of the following epithelial ovarian cancer cell lines: SKOV-3 and ES-2 (American Type Culture Collection).

As described in Example 1, after culturing for about 24 to 72 hours, beads with a monolayer of cells were observed. These positive beads were isolated and the amino acid sequence of each positive bead was determined, as described in Example 1.

The following ligands for cells of the SKOV-3 cell line were identified:

cdGIGPQc; c-d-G-Phg-G-P-F-c; c-d-G-Cit-G-Hyp(Bzl)-M-c;

c-d-G-Phe(4-Me)-G-T-Pra-c; cdGLGFTc; c-d-G-Nva-G-Phe (4-CN)-F-c;

c-d-G-Tyr(3NO$_2$)-G-Pra-G-c; c-d-G-(4-Pal)-G-Tyr(3-NO$_2$)-Cha-c; and c-d-G-Cha-G-1-T-c.

The following ligands for cells of the ES-2 cell line were identified:

c-d-G-V-G-Hyp-HoSer-c; c-d-G-Phe(4Me)-G-P-Cha-c; c-d-G-Phe(3-Cl)-G-Q-F-c;

cdGLGYYc; c-d-G-L-G-HoSer-T-c; c-d-G-Tyr(Me)-G-T-M-c; and c-d-G-Cha-G-HoCit-S-c.

EXAMPLE 4

The method as described in Example 1 was performed, except that a different combinatorial library was used and different types of epithelial cancer cells were used. The peptide library of Example 3 was used, except that the concentration of peptides on the surface of each bead was 20% of that used in Example 3, resulting in an increase in screening stringency.

The peptide library was screened with one of the following epithelial ovarian cancer cell lines: CaOV3, SKOV-3, ES-2 and OVCAR-3 (American Type Culture Collection).

As described in Example 1, after culturing for about 24 to 72 hours, beads with a monolayer of cells were observed. These positive beads were isolated and the amino acid sequence of each positive bead was determined, as described in Example 1.

The following ligands for cells of the CaOV3 cell line were identified:
cdGMGSAc; c-d-G-M-G-S-Cha-c; c-d-G-M-G-HoSer-Nle-c;
c-d-G-Tyr(3-$NO_2$)-G-i-Pra-c; c-d-G-Tyr(3-$NO_2$)-G-F-L-c; c-d-G-Chg-G-Hyp-N-c; and
c-D-G-Cha-G-Hyp-N-c.

The following ligands for cells of the SKOV-3 cell line were identified:
c-d-G-A-G-Bta-L-c; c-d-G-L-G-S-Bpa-c; c-d-G-Nle-G-Phe(3-Cl)-S-c;
c-d-G-Tyr(3-$NO_2$)-G-Phg-M-c; and c-d-G-Tyr(3-$NO_2$)-G-Nle-H-c.

The following ligands for cells of the ES-2 cell line were identified:
c-d-G-Aib-G-P-S-c; c-d-G-Cha-G-Bta-Q-c; c-d-G-Bta-G-Hyp-Y-c;
c-d-G-Phe(4-Me)-G-Aib-S-c; c-d-G-Aib-G-Aib-N-c; cdG-LGWGc;
c-d-G-Cha-G-HoCit-Q-c; and c-d-G-HoCit-G-P-Q-c.

The following ligands for cells of the OVCAR-3 cell line were identified:
c-d-G-Phe(3-Cl)-G-T-Y-c; c-d-G-Tyr(3-$NO_2$)-G-Aic-Q-c;
c-Tyr(3-$NO_2$)-G-F-G-(Pal-3D)-HoSer-c; c-d-G-HoCit-G-T-Nva-c; c-d-G-Nle-G-1-G-c;
and c-Nle-G-Nle-G-Tyr(3-$NO_2$)-L-c.

EXAMPLE 5

The method as described in Example 1 was performed, except that a different combinatorial library was used and non-epithelial cancer cells were used. A one-bead-one-compound combinatorial peptide library was prepared as described in Example 3.

The peptide library was screened with the non-epithelial glioblastoma brain cancer cell line A-172 (American Type Culture Collection).

As described in Example 1, after culturing for about 24 to 72 hours, beads with a monolayer of cells were observed. These positive beads were isolated and the amino acid sequence of each positive bead was determined, as described in Example 1.

The following ligands were identified: cDGLGDDc; cDGWGPNc; c-N-G-Nle-G-(4-Pal)-M-c; c-e-G-y-G-Hyp-W-c; c-d-G-(4-Pal)-G-Phe (4-Me)-T-c; c-e-G-N-G-S-(1-Nal)-c; c-D-G-L-G-P-HoPhe-c; and c-e-G-L-G-Nle-M-c.

EXAMPLE 6

The method as described in Example 1 was performed, except that a different combinatorial library was used and a different cell type was used. A one-bead-one-compound combinatorial library consisting of small molecules was prepared according to the method described in Liu et al., "A novel peptide-based encoding system," 7678-7680. The library consisted of molecules of the general structure

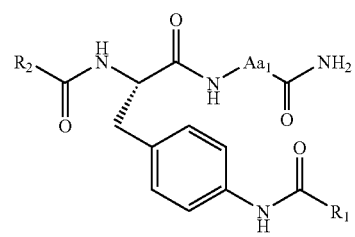

where "$Aa_1$" was one of 96 amino acids including 20 L-natural amino acids and 19 D-isomers, 15 beta-amino acids, and 42 other amino acids; "$R_1COOH$" was one of 33 carboxylic acids, acyl chlorides, or sulfonyl chlorides; and "$R_2COOH$" was one of 50 carboxylic acids; as described in Liu et al., "A novel peptide-based encoding system," 7678-7680.

The small molecule library was screened with the liver cancer cell line HEPG2 (American Type Culture Collection).

As described in Example 1, after culturing for about 24 to about 72 hours, beads with a monolayer of cells were observed. These positive beads were isolated as described in Example 1. The chemical structure of the small molecule on each positive bead was determined according to the method described in Liu et al., "A novel peptide-based encoding system," 7678-7680.

Ligands having the general structure

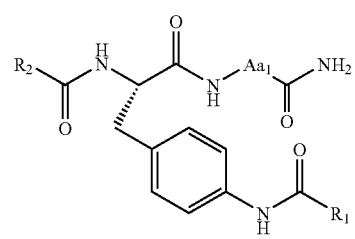

were identified, where "$Aa_1$" was D-cys, Cys, Trp, Nva, Aic, Dpr, Ile, Nle, or D, L-beta-Fal(2); "$R_1COOH$" was 3-pyridine propionic acid, 4-bromophenyl acetic acid, 2-pyrazine carboxylic acid, 2-thiophene carboxylic acid, phenoxy acetic acid, benzoic acid, or cyclopropane carboxylic acid; and "$R_2COOH$" was indole-2-carboxylic acid, 4-phenoxybenzoic acid, 2-butynoic acid, 2-pyrazine carboxylic acid, 4-hydroxyl phenyl acetic acid, or 3-thiophene carboxylic acid. The structure of twelve of the ligands is shown in Tables 1 and 2.

TABLE 1

Liver Cancer Cell Ligands (HEPG2 cells)

| Entry | Aa₁ | Structure | R₁ COOH | Structure | R₂ COOH | Structure |
|---|---|---|---|---|---|---|
| 1 | cys | H₂N-CH(COOH)-CH₂-SH | 3-Pyridine propionic acid | pyridin-3-yl-CH₂CH₂-COOH | Indole-2-carboxylic acid | indole-2-COOH |
| 2 | cys | H₂N-CH(COOH)-CH₂-SH | 4-Bromophenyl acetic acid | 4-Br-C₆H₄-CH₂-COOH | 4-Phenoxy benzoic acid | 4-PhO-C₆H₄-COOH |
| 3 | Cys | H₂N-CH(COOH)-CH₂-SH | 2-Pyrazine carboxylic acid | pyrazine-2-COOH | 4-Phenoxy benzoic acid | 4-PhO-C₆H₄-COOH |
| 4 | Cys | H₂N-CH(COOH)-CH₂-SH | 2-Thiophene carboxylic acid | thiophene-2-COOH | 2-Butynoic acid | H₃C-C≡C-COOH |
| 5 | Cys | H₂N-CH(COOH)-CH₂-SH | Phenoxy acetic acid | Ph-O-CH₂-COOH | 2-Pyrazine carboxylic acid | pyrazine-2-COOH |
| 6 | Trp | H₂N-CH(COOH)-CH₂-(indol-3-yl) | Phenoxy acetic acid | Ph-O-CH₂-COOH | 2-Pyrazine carboxylic acid | pyrazine-2-COOH |
| 7 | Nva | H₂N-CH(COOH)-CH₂CH₂CH₃ | Phenoxy acetic acid | Ph-O-CH₂-COOH | 4-Phenoxy benzoic acid | 4-PhO-C₆H₄-COOH |
| 8 | Aic | 2-amino-indane-2-carboxylic acid | Phenoxy acetic acid | Ph-O-CH₂-COOH | 4-Hydroxyl phenyl acetic acid | 4-HO-C₆H₄-CH₂-COOH |
| 9 | Dpr | H₂N-CH(COOH)-CH₂-NH₂ | Benzoic acid | Ph-COOH | 4-Hydroxyl phenyl acetic acid | 4-HO-C₆H₄-CH₂-COOH |

TABLE 1-continued

Liver Cancer Cell Ligands (HEPG2 cells)

| Entry | Aa₁ | Structure | R₁ COOH | Structure | R₂ COOH | Structure |
|---|---|---|---|---|---|---|
| 10 | Ile | 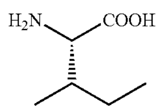 | Cyclopropane carboxylic acid | 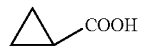 | 3-Thiophene carboxylic acid | 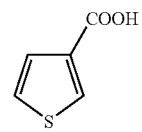 |
| 11 | Nle | 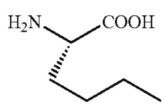 | 4-Bromophenyl acetic acid | 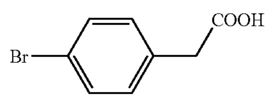 | 3-Thiophene carboxylic acid | 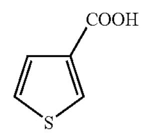 |
| 12 | D,L-beta-Fal(2) | 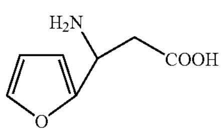 | 3-Pyridine propionic acid | 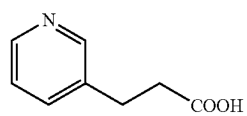 | 3-Thiophene carboxylic acid | 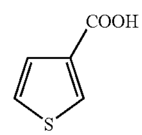 |

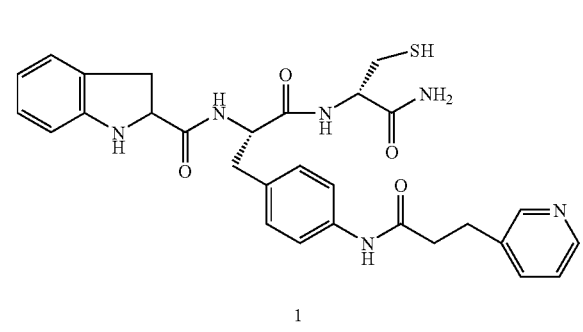

TABLE 2

Chemical Structure of Ligands for Liver Cancer Cells (HEPG2)

1

2

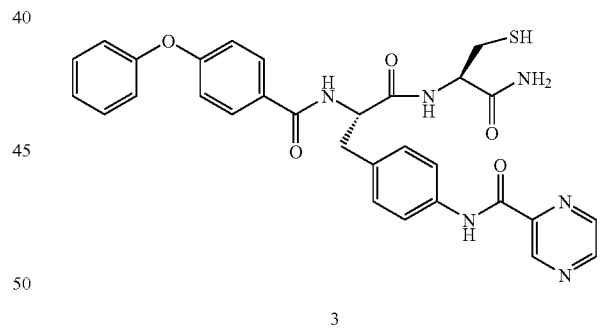

TABLE 2-continued

Chemical Structure of Ligands for Liver Cancer Cells (HEPG2)

3

4

TABLE 2-continued

Chemical Structure of Ligands for Liver Cancer Cells (HEPG2)

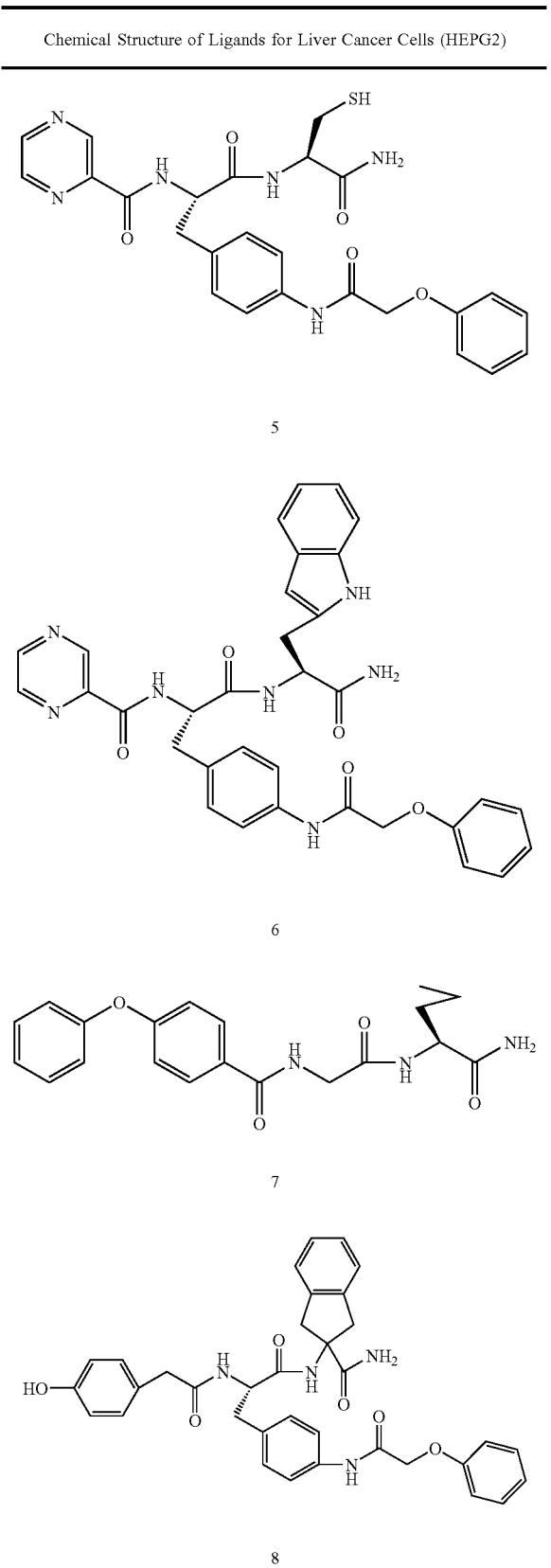

5

6

7

8

TABLE 2-continued

Chemical Structure of Ligands for Liver Cancer Cells (HEPG2)

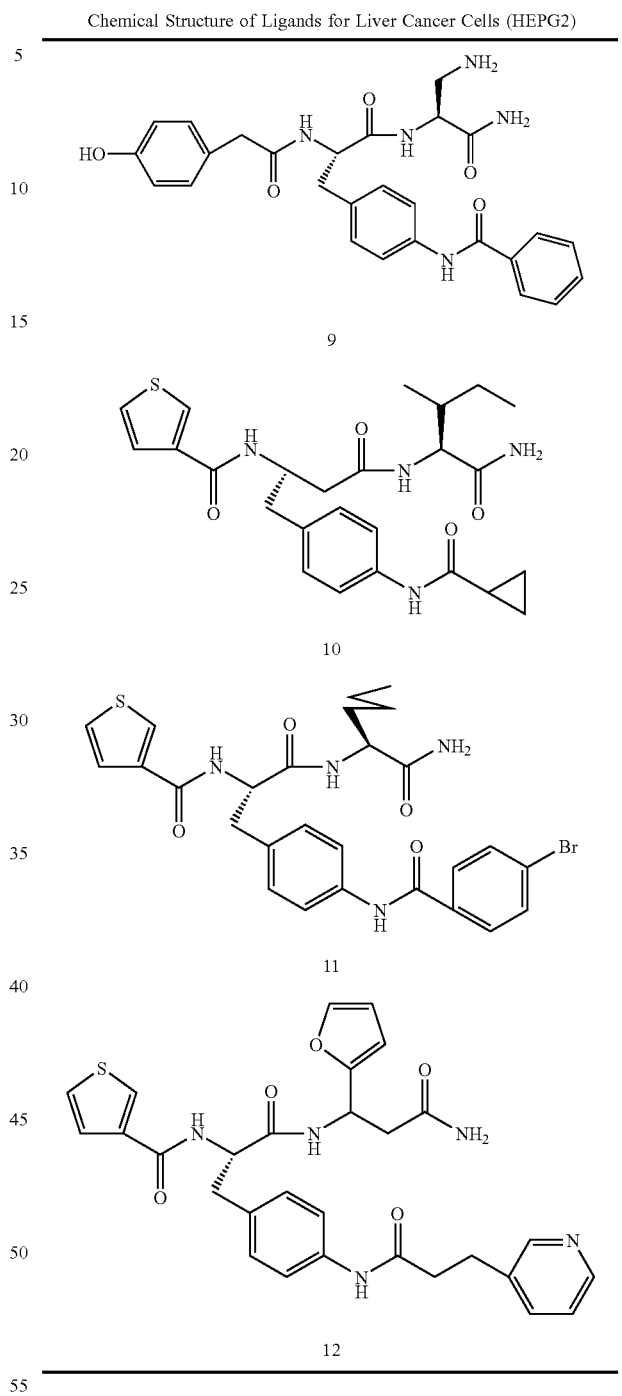

9

10

11

12

EXAMPLE 7

The method as described in Example 1 was performed, except that a different combinatorial library was used. A one-bead-one-compound combinatorial peptidomimetic or modified peptide library of the chemical structure cNGZ$_2$GZ$_1$Xc was prepared. "X" was Pro, Ala, Gly, Leu, Ile, Asp, Asn, Glu, Gln, Trp, His, Phe, Tyr, Val, Ser, Thr or Met; "Z$_1$" was Y, Nle, E, T, Phe(NHR$_1$), or Phe(NHR$_1$,); and "Z$_2$" was Nle, H, D, Q, Phe(NHR$_2$), or Phe(NHR$_2$). "R1" was benzoic acid, 5-bromovaleric acid, 3-pyridinepropionic acid, 3-thiophenecarboxylic acid, 4-(dimethylamino)phenylacetic acid, 4-bromobenzoic acid, phenoxyacetic acid, (1-aphtoxy)acetic acid, 5-hydantoinacetic acid, phenylpropionic acid, cyclopropanecarboxylic acid, 4-methyvaleric acid, 2-phenoxybutyric acid, 3-(dimethylamino)benzoic acid, 3-thiophenecarboxylic acid, 2-pyrazinecarboxylic acid, furylacrylic acid, 3,4-dichlorophenylacetic acid, 3-indolepropionic acid, 2,5-dimethoxyphenylacetic acid, 3-hydroxy-2-quinoxalinecarboxylic acid, 4-hydrxyphenylacetic acid, cyclohexanecarboxylic acid, 2-methylbutyric acid, or 4-bromophenylacetic acid; "$R_1$," was p-toluensulfonyl chloride, 3,4-dimethoxybenzoyl chloride, 2-naphtalenesulfonyl chloride, 2-thiphenesulfonyl chloride, 2-thiopheneacetyl chloride, or propargylchloroformate; "$R_2$" was benzoic acid, 5-bromovaleric acid, 3-pyridinepropionic acid, 3-thiophenecarboxylic acid, 4-(dimethylamino)phenylacetic acid, 4-bromobenzoic acid, phenoxyacetic acid, (1-naphtoxy)acetic acid, 5-hydantoinacetic acid, phenylpropionic acid, cyclopropanecarboxylic acid, 4-methyvaleric acid, 2-phenoxybutyric acid, 3-(dimethylamino)benzoic acid, 3-thiophenecarboxylic acid, 2-pyrazinecarboxylic acid, furylacrylic acid, 3,4-dichlorophenylacetic acid, 3-indolepropionic acid, 2,5-dimethoxyphenylacetic acid, 3-hydroxy-2-quinoxalinecarboxylic acid, 4-hydrxyphenylacetic acid, cyclohexanecarboxylic acid, 2-methylbutyric acid, 4-bromophenylacetic acid, or 4-nitrophenylacetic acid; and "$R_2$," was p-toluensulfonyl chloride, 3,4-dimethoxybenzoyl chloride, 2-naphtalenesulfonyl chloride, 2-thiphenesulfonyl chloride, 2-thiopheneacetyl chloride, or propargylchloroformate.

The peptidomimetic library was synthesized on 4 g of TentaGel S $NH_2$ resin (0.26 mmol/g, Rapp Biopolymere) with standard solid phase peptide synthesis methods, using a split-mix synthesis approach. The coupling of all Fmoc protected amino acids (3eq) was initiated by DIC (3eq), HOBt (3eq) and the progress of the reaction was monitored by the Kaiser test. The Fmoc protecting groups were removed by 20% piperidine in DMF (2×10 min).

D-Cys was first coupled to the resin in the first cycle. In the second cycle, 17 natural amino acids (X) were then added. In the third cycle, the resins were divided up into 5 portions (v:v:v:v:v=1:1:1:1:32) and Tyr, Nle, Glu, Thr, and Phe(4-$NO_2$) were added to the respective resin portion together with the coupling reagents. After coupling was completed, the Phe(4-$NO_2$) resin was treated with 2M $SnCl_2$ in DMF (24 hrs) to transform the nitrogroup to an amino group. The resin was then divided into 32 portions. 26 acids ($R_1$, 20eq) and 6 acyl or sulfonyl chlorides ($R_1$, 20eq) were coupled to the side chain of the aminophenylalanine. DIC (20eq) plus DIEA (10eq) was used as coupling reagents for the former, and DIEA (10eq) was used as coupling reagent for the latter. In the fourth cycle, Gly was attached. The fifth cycle was carried out according to the method used in the third cycle, with the following amino acids: Nle, His, Asp, Gln, or Phe(4-$NO_2$). After the nitro group of Phe(4-$NO_2$) was reduced to amino group, 27 acids ($R_2$) and 6 chlorides ($R_2$,) were added. Finally, the last three amino acids were coupled and the side chain protecting groups were removed by TFA:TIS:water:EDT (94:1:2.5:2.5 v/v/v/v, 3 hrs). The library was then thoroughly washed and the disulfide bridge was formed by air oxidation for 48 hrs mediated by DMSO (10%). The library was washed and stored in 70% ethanol.

The peptidomimetic library was screened with the non-small-cell lung cancer cell line A549 (American Type Culture Collection).

As described in Example 1, after culturing for about 24 to 72 hours, beads with a monolayer of cells were observed. These positive beads were isolated and the chemical structure of the peptidomimetic compound on each positive bead was determined using amino acid sequencing, as described in Example 1.

Ligands having the general structure $cNGZ_2GZ_1Xc$ were identified, where "X", "$Z_1$", and "$Z_2$" were as set forth above. The structure of ten of the ligands is shown in Table 3.

TABLE 3

Chemical Structure of Ligands for
Non-Small-Cell Lung Cancer Cells (A549)
c-N-G-$Z_2$-G-$Z_1$-X-c

| $Z_2$ | $Z_1$ | X |
|---|---|---|
| [structure: H$_2$N-CH(COOH)-CH$_2$-C$_6$H$_4$-NH-SO$_2$-C$_6$H$_4$-CH$_3$ (p-toluenesulfonamide of aminophenylalanine)] | [structure: H$_2$N-CH(COOH)-CH$_2$-CH$_2$-COOH (Glu)] | [structure: H$_2$N-CH(COOH)-CH$_2$-indole (Trp)] |
| [structure: H$_2$N-CH(COOH)-CH$_2$-C$_6$H$_4$-NH-C(O)-pyrazine (pyrazinecarboxamide of aminophenylalanine)] | [structure: H$_2$N-CH(COOH)-CH$_2$-CH$_2$-COOH (Glu)] | [structure: H$_2$N-CH(COOH)-CH$_2$-CH$_2$-CONH$_2$ (Gln)] |

TABLE 3-continued
Chemical Structure of Ligands for
Non-Small-Cell Lung Cancer Cells (A549)
c-N-G-$Z_2$-G-$Z_1$-X-c
| $Z_2$ | $Z_1$ | X |
|---|---|---|
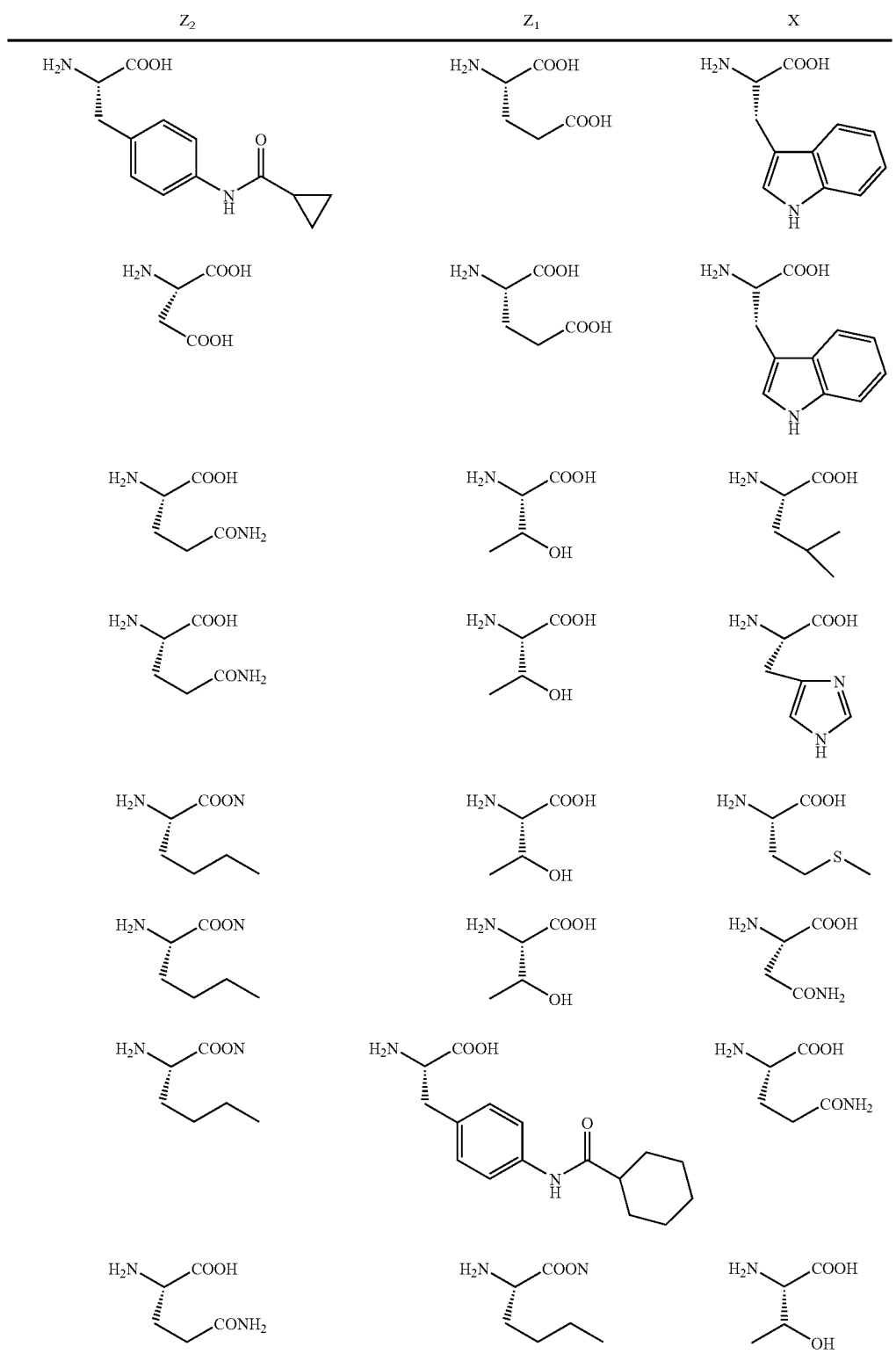

EXAMPLE 8

The method as described in Example 7 was performed, except that the peptidomimetic library was screened with the pancreatic cancer cell line Panc-1 (American Type Culture Collection).

As described in Example 1, after culturing for about 24 to 72 hours, beads with a monolayer of cells were observed. These positive beads were isolated and the chemical structure of the peptidomimetic compound on each positive bead was determined using amino acid sequencing, as described in Example 1.

Ligands having the general structure $cNGZ_2GZ_1Xc$ were identified, where "X", "$Z_1$", and "$Z_2$" were as set forth in Example 7. Six of these ligands are shown in Table 4.

TABLE 4

Chemical Structure of Ligands
for Pancreatic Cancer Cells (Panc-1)
$c\text{-}N\text{-}G\text{-}Z_2\text{-}G\text{-}Z_1\text{-}X\text{-}c$

| $Z_2$ | $Z_1$ | X |
|---|---|---|

TABLE 4-continued

Chemical Structure of Ligands
for Pancreatic Cancer Cells (Panc-1)
c-N-G-$Z_2$-G-$Z_1$-X-c

| $Z_2$ | $Z_1$ | X |
|---|---|---|
| (structure: H₂N-CH(COOH)-CH₂-C₆H₄-NH-C(O)-thiophen-3-yl) | (structure: H₂N-CH(COOH)-CH₂-C₆H₄-NH-C(O)-C₆H₄-N(CH₃)₂) | (structure: H₂N-CH(COOH)-CH₂-CONH₂) |

The invention has been described above with reference to the preferred embodiments. Those skilled in the art may envision other embodiments and variations of the invention that fall within the scope of the claims.

We claim:

1. A ligand specific for human epithelial cancer cells, wherein said ligand has the chemical structure of cDG-LGDDc.

2. A ligand specific for human epithelial cancer cells, wherein said ligand has the chemical structure of c-d-G-HoCit-G-P-Q-c.

3. A ligand specific for human non-epithelial cancer cells, wherein said ligand has the chemical structure of cDG-LGDDc.

* * * * *